United States Patent [19]

Mitsuda et al.

[11] Patent Number: 4,607,013

[45] Date of Patent: Aug. 19, 1986

[54] BIOCHEMICAL PROCESS FOR OPTICAL RESOLUTION OF CYCLOPENTENOLONE DERIVATIVES

[75] Inventors: Satoshi Mitsuda; Hideo Hirohara, both of Osaka, Japan

[73] Assignee: Sumitomo Chemical Company, Limited, Osaka, Japan

[21] Appl. No.: 646,809

[22] PCT Filed: Mar. 18, 1983

[86] PCT No.: PCT/JP83/00086

§ 371 Date: Sep. 7, 1984

§ 102(e) Date: Sep. 7, 1984

[87] PCT Pub. No.: WO84/03714

PCT Pub. Date: Sep. 27, 1984

[51] Int. Cl.$^4$ .......................... C07P 41/00; C12P 7/38
[52] U.S. Cl. ..................................... 435/280; 435/149
[58] Field of Search ................................ 435/149, 280

[56] References Cited

U.S. PATENT DOCUMENTS 4,385,186  5/1983  Matsuo et al. ...................... 568/379

FOREIGN PATENT DOCUMENTS 50-15843  6/1975  Japan .
0047495   3/1983  Japan ................................. 435/149

OTHER PUBLICATIONS

Oritani et al., *Agr. Biol. Chem.* 38(10), 1961–1964, (1974).
Chemical Abstracts I: 85: 61429y Mar. 25, 76.
Iriuchuima, S. et al., *Agric. Biol. Chem.*, 45(6) pp. 1389–1392, 1981.

*Primary Examiner*—Sidney Marantz
*Assistant Examiner*—L. Krawczewicz
*Attorney, Agent, or Firm*—Sughrue, Mion, Zinn, Macpeak, and Seas

[57] ABSTRACT

A biochemical process for optical resolution of 4-hydroxy-3-methyl-2-2'-propynyl-2-cyclopentenone, which comprises asymmetrically hydrolyzing organic carboxylic acid (saturated or unsaturated carboxylic acids having 1 to 18 carbon atoms) esters of (±)-4-hydroxy-3-methyl-2-2'-propynyl-2-cyclopentenone by the action of an esterase originated from a microorganism or an animal pancreas to give optically active 4-hydroxy-3-methyl-2-2'-propynyl-2-cyclopentenone and esters of its antipode with high optical purity is disclosed. This resolution process is simple in steps as compared with the conventionally known organic chemical methods of optical resolution, and is quite advantageous industrially because it does not require expensive optically active reagents.

5 Claims, No Drawings

BIOCHEMICAL PROCESS FOR OPTICAL RESOLUTION OF CYCLOPENTENOLONE DERIVATIVES

THE TECHNICAL FIELD

This invention relates to a biochemical process for optical resolution of (±)-4-hydroxy-3-methyl-2-2'-propynyl-2-cyclopentenone represented by the following formula (I):

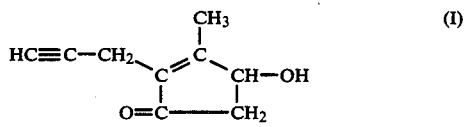

More particularly, the invention relates to an industrially advantageous biochemical process for optical resolution of 4-hydroxy-3-methyl-2-2'-propynyl-2-cyclopentenone, which comprises asymmetrically hydrolyzing organic carboxylic acid (saturated or unsaturated carboxylic acids having 1 to 18 carbon atoms) esters of (±)-4-hydroxy-3-methyl-2-2'-propynyl-2-cyclopentenone by the action of an esterase originated from a microorganism or an animal pancreas to give optically active 4-hydroxy-3-methyl-2-2'-propynyl-2-cyclopentenone and esters of its antipode with high optical purity.

BACKGROUND TECHNOLOGY

4-Hydroxy-3-methyl-2-2'-propynyl-2-cyclopentenone (hereinafter referred to as propynylcyclopentenolone) is known as one of the important alcohol components in a group of ester compounds called "synthetic pyrethroids" which have excellent insecticidal activities.

For example, a compound of the formula (II) as described below which is an ester of the propynylcyclopentenolone and 2,2,3,3-tetramethylcyclopropanecarboxylic acid is an excellent insecticide having quite strong knockdown and lethal effects (Japanese Published Examined Patent Application No. 50-15843).

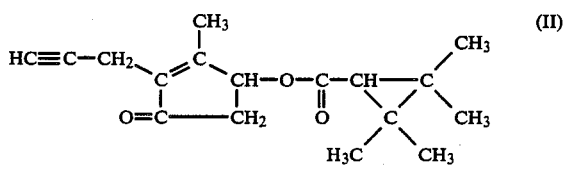

There are two kinds of optical isomers in the propynylcyclopentenolone because it has an asymmetric carbon atom in the 4-position thereof, and usually, their activities as esters are greatly different. For example, in the ester represented by the foregoing formula (II), an ester of the (+)-propynylcyclopentenolone has an insecticidal activity several times higher than that of a corresponding ester of the (−)-propynylcyclopentenolone. Thus, there are demanded industrially advantageous technologies of optical resolution of the (±)-propynylcyclopentenolone obtained by the conventional production processes.

As methods for producing optically active propynylcyclopentenolone, a following method has been known; which method comprises converting (±)-propynylcyclopentenolone into a half ester of phthalic acid, reacting this ester with an optically active amine to form diastereomer salts of the optically active propynylcyclopentenolone, isolating and recovering a salt as the amine used and half ester, and then, hydrolyzing the resulting half ester (Japanese Published Unexamined Patent Application No. 56-2929). It is hard to say that this process is satisfactory, however, because it is low in overall yield and requires complicated procedures and expensive optically active reagents.

DISCLOSURE OF THE INVENTION

The present inventors have conducted extensive studies in order to establish a process for optical resolution of (±)-propynylcyclopentenolone, which may overcome the foregoing problems and is more advantageous industrially. As a result, the present inventors have found that optically active propynylcyclopentenolone and esters of its antipode having high optical purity can be obtained by reacting the organic carboxylic acid (saturated or unsaturated organic carboxylic acids having 1 to 18 carbon atoms) esters of (±)-propynylcyclopentenolone with an esterase originated from a microorganism or an animal pancreas. The present invention has been achieved by giving various considerations to such finding.

Hereunder, the present invention will be explained in detail. Organic carboxylic acid (saturated carboxylic acids having 1 to 18 carbon atoms) esters of (±)-propynylcyclopentenolone used as the starting material in the process of the present invention can be easily prepared by conventional methods for the production of esters, e.g., a method for reacting (±)-propynylcyclopentenolone with anhydrides of organic carboxylic acids, a method for reacting it with organic carboxylic acid chlorides in the presence of organic bases, or the like.

The microorganisms, which produce employable esterase in the invention, are those capable of asymmetrically hydrolyzing the organic carboxylic acid esters of (±)-propynylcyclopentenolone and are not particularly restricted in the origin. (In this specification, the term "esterase" means an esterase in a broad sense, including lipase.) As the examples of such microorganisms, the following genuses may be illustrated: Enterobacter, Arthrobacter, Brevibacterium, Pseudomonas, Alcaligenes, Flavobacterium, Micrococcus, Chromobacterium, Mycobacterium, Corynebacterium, Bacillus, Lactobacillus, Trichoderma, Candida, Saccharomyces, Rhodotorula, Cryptococcus, Torulopsis, Pihia, Penicillium, Aspergillus, Rhizopus, Mucor, Aureobasidium, Actinomucor, Nocardia, Streptomyces.

Names of typical strains belonging to the respective genera are illustrated below, but the microorganisms of the present invention are not limited to these illustrative examples.

| | | | |
|---|---|---|---|
| (1) | *Enterobacter cloacae* | IFO | 3320 |
| (2) | *Arthrobacter simplex* | IFO | 3530 |
| (3) | *Brevibacterium ammoniagenes* | IFO | 12072 |
| (4) | *Pseudomonas fluorescens* | IFO | 3081 |
| (5) | *Alcaligenes faecalis* | IFO | 12669 |
| (6) | *Flavobacterium arborescens* | IFO | 3750 |
| (7) | *Micrococcus luteus* | OUT | 8276 |
| (8) | *Chromobacterium viscosum* | ATCC | 6918 |
| (9) | *Mycobacterium phlei* | IFO | 3158 |
| (10) | *Corynebacterium equi* | ATCC | 7699 |
| (11) | *Bacillus subtilis* | IFO | 3026 |
| (12) | *Lactobacillus casei* | IFO | 3322 |
| (13) | *Trichoderma viride* | IFO | 4847 |
| (14) | *Saccharomyces rouxii* | IFO | 0505 |

| | | |
|---|---|---|
| (15) Candida utilis | IFO | 0396 |
| (16) Rhodotorula minuta | IFO | 0879 |
| (17) Cryptococcus albidus | IFO | 0378 |
| (18) Torulopsis candida | IFO | 0768 |
| (19) Pihia polimorpha | IFO | 1166 |
| (20) Penicillium frequentans | IFO | 5692 |
| (21) Aspergillus var asper | IFO | 5324 |
| (22) Rhizopus chinensis | IFO | 4737 |
| (23) Aureobasidium pullulans | IFO | 4464 |
| (24) Actinomucor elegans | IFO | 4022 |
| (25) Nocardia asteroides | IFO | 3424 |
| (26) Streptomyces griseus | IFO | 3356 |
| (27) Mucor javanicus | IFO | 4572 |

All of these strains are deposited in American Type Culture Collection (ATCC), Osaka University, Faculty of Engineering, Department of Fermentation Technology (OUT), or Institute of Fermentation, Osaka (IFO) and are available from these depositories.

Such microorganisms may be cultured in a liquid medium to obtain a cultured medium according to the conventional procedures. For example, a microorganism may be inoculated to a sterilized liquid medium [for fungi and yeasts, a malt extract-yeast extract medium (5.0 g of peptone, 10.0 g of glucose, 3.0 g of malt extract and 3.0 g of yeast extract dissolved in 1 l of water and adjusted to pH 6.5), and for bacteria, a sugar-added bouillon medium (10.0 g of glucose, 5.0 g of peptone, 5.0 g of meat extract and 3.0 g of NaCl dissolved in 1 l of water and adjusted to pH 7.2)], and subjected to a shaken culture ordinarily at a temperature of 20° to 40° C. for 2 to 3 days. In addition, if necessary, it may be cultured on a solid medium.

In the present invention, among the above-described microorganisms, those belonging to the genera Enterobacter, Arthrobacter, Brevibacterium, Pseudomonas, Alcaligenes, Chromobacterium, Mycobacterium, Bacillus, Trichoderma, Candida, Rhodotorula, Torulopsis, Aspergillus, Rhizopus, Mucor, Nocardia and Streptomyces are particularly preferable in view of the esterase activity and asymmetric yield.

Some of the esterases originated from these microorganisms are commercially available. Specific examples of such esterases include a lipase from the Pseudomonas sp. (made by Amano Seiyaku Co., Ltd.), lipase from the Aspergillus sp. (Lipase AP, made by Amano Seiyaku Co., Ltd.), lipase from the Mucor sp. (Lipase M-AP, made by Amano Seiyaku Co., Ltd.), lipase from *Candida cylindracea* (Lipase MY, made by Meito Sangyo Co., Ltd.), lipase from the Alcaligenes sp. (Lipase PL, made by Meito Sangyo Co., Ltd.), lipase from the Achromobacter sp. (Lipase AL, made by Meito Sangyo Co., Ltd.), lipase from the Arthrobacter sp. (Lipase Godo BSL, made by Godo Shusei Co., Ltd.), lipase from the Chromobacterium sp. (made by Toyo Jozo Co., Ltd.), lipase from *Rhizopus delemar* (Talipase, made by Tanabe Seiyaku Co., Ltd.) and lipase from the Rhizopus sp. (Lipase Saiken, made by Osaka Saikin Kenkyusho).

In addition, steapsin and pancreatin can be used as the animal-origin pancreatic esterase.

THE BEST MODE FOR EMBODIMENT OF THE INVENTION

In practicing the process of the present invention, the asymmetric hydrolysis of organic carboxylic acid (saturated or unsaturated carboxylic acids having 1 to 18 carbon atoms) ester of (±)-propynylcyclopentenolone is carried out by stirring or shaking a mixture of said ester and an esterase-containing liquor, such as cultured liquor of such microorganisms, microorganism cells separated from the cultured liquor, esterase-containing culture filtrates, crude or purified esterases or esterase-containing extracts or concentrates separated from microorganism cells or culture filtrates by various enzymatic separation procedures, or aqueous solution containing esterase originated from animal pancrease. Alternatively, the microorganism cell or the esterase may be used in an immobilized state.

For the conditions of conducting the asymmetric hydrolysis of the organic carboxylic acid esters of (±)-propynylcyclopentenolone, a suitable reaction temperature is 10° to 70° C., preferably 50° to 65° C. for cultured media of thermophilic bacteria or thermostable esterases obtained by culture of thermophilic bacteria, and 20° to 50° C. for cultured media of mesophilic bacteria or esterases having no thermostability.

The reaction time is usually 3 to 48 hours, but it can be shortened by elevating the reaction temperature or by increasing the amount of esterases.

It is preferred that the pH value during the reaction is 8 to 11 for cultured media of alkalophilic bacteria or alkaline esterases, and 5 to 8 for cultured media of non-alkalophilic microorganisms or esterases having no stability to alkali. In addition, use of buffer solutions is preferred in order to neutralize the organic carboxylic acids formed by the hydrolysis to keep the pH value during the reaction constant. Buffer solutions of inorganic acid salts such as sodium phosphate, potassium phosphate, etc., and those of organic acid salts such as sodium acetate, sodium citrate, etc., can be used.

The concentration of the organic carboxylic acid esters of (±)-propynylcyclopentenolone used for the substrate is 1 to 50 wt%, preferably 5 to 25 wt%, to the reaction mixture.

After such asymmetric hydrolysis reaction, obtained optically active free propynylcyclopentenolone and unreacted antipode ester are separated from each other and recovered. In the separating and recovering, such procedures can be employed as steam distillation, solvent extraction, fractional distillation, column chromatography, and the like. For example, the reaction mixture is steam distilled, followed by extraction of the distillate with diethyl ether, or directly extracted with organic solvents such as diethyl ether, ethyl acetate, benzene, etc. The extract is then subjected to fractional distillation to isolate optically active propynylcyclopentenolone from an ester of its antipode, or to silica gel column chromatography. The chromatography procedures are carried out by, for example, first isolating an organic carboxylic acid ester of optically active propynylcyclopentenolone by eluting with a toluene-ethyl acetate (5:1) solution, and then isolating the antipode free propynylcyclopentenolone by eluting with a toluene-ethyl acetate (2:1) solution.

The ester of optically active propynylcyclopentenolone thus separated can be easily introduced into optically active propynylcyclopentenolone by further deacylation. The reaction of deacylation is carried out by, for example, adding water and an equivalent amount of sodium hydrogencarbonate to the organic carboxylic acid ester of propynylcyclopentenolone, further adding a 10% HCl aqueous solution to adjust to pH 5, and subsequently refluxing with stirring for 8 hours, whereby propynylcyclopentenolone can be readily obtained.

As described above in detail, the optical resolution of (±)-propynylcyclopentenolone according to the process of the present invention is simple in steps as compared with the conventional method of organic chemical optical resolution, and is economically advantageous because of its no requirement for expensive optically active reagents.

Moreover, the process of the invention is quite advantageous industrially because it gives optically active propynylcyclopentenolone with high yield and optical purity.

The present invention will be described in further detail by reference to the following examples, but it is not limited thereto.

EXAMPLES 1 TO 8

1.0 g of an acetic acid ester of (±)-propynylcyclopentenolone and 20 mg of each esterase as shown in Table 1 were added to 10 ml of a buffer solution (McIlvaine buffer solution of pH 7.0 or 0.2M $Na_2CO_3$—$NaHCO_3$ buffer solution of pH 9.5) and allowed to react at 30° C. with vigorous stirring using an agitator. After 24 hours of the reaction, the reaction product was extracted with ethyl acetate. The extract was analyzed by gas chromatography (5% DEGS, 1.1 m, 180° C.), and a hydrolysis rate was calculated from the peak area ratio of propynylcyclopentenolone to its acetic acie ester. The results are shown below. The extract was concentrated, subjected to silica gel column chromatography and eluted with a toluene-ethyl acetate (5:1) solution to isolate an unreacted acetic acid ester of propynylcyclopentenolone, which was then further eluted with a toluene-ethyl acetate (2:1) solution to obtain free propynylcyclopentenolone.

10 mg of the free propynylcyclopentenolone thus obtained was dissolved in 1 ml of toluene, and 0.2 ml of pyridine and 45 mg of (−)-α-methoxy-α-trifluoromethylphenylacetic chloride ((−)-MTPA chloride) were added thereto, followed by refluxing under heating for 1 hour to obtain a (−)-MTPA-diastereomer of propynylcyclopentenolone. This was then subjected to optical isomeric analysis by gas chromatography (Silicon DCQF-1, 30 m capillary columns, 180° C.), and the optical isomer form and optical purity of the free propynylcyclopentenolone were determined from the peak area ratio of the diastereomer of (+)-propynylcyclopentenolone to that of (−)-propynylcyclopentenolone.

Meanwhile, to the unreacted ester obtained by the column chromatography procedure were added 5 ml of water and an equivalent amount, to the ester, of sodium hydrogencarbonate, and further added a 10% HCl aqueous solution to adjust to pH 5, followed by deacylating by refluxing with stirring for 8 hours. After cooling, ethyl acetate, water and NaCl were added to the reaction mixture to thereby effect extraction. After distilling away the solvent, a thus-obtained oily material was subjected to silica gel column chromatography and eluted with a toluene-ethyl acetate (2:1) solution to obtain optically active propynylcyclopentenolone.

The propynylcyclopentenolone was analyzed for the optical isomer ratio by gas chromatography as described above to determine the optical isomer form and optical purity of the unreacted ester. The results are shown in Table 1.

TABLE 1

| Example No. | Origin of Esterase | Hydrolysis Rate (%) | Free Propynylcyclopentenolone Optical Isomer Form | Free Propynylcyclopentenolone Optical Purity (%) | Unreacted Ester Optical Isomer Form | Unreacted Ester Optical Purity (%) |
|---|---|---|---|---|---|---|
| 1 | Arthrobacter sp. (Lipase Godo BSL) | 50.0 | (−) | 100 | (+) | 100 |
| 2 | Pseudomonas sp. | 50.0 | (−) | 100 | (+) | 100 |
| 3 | Achromobacter sp. (Lipase AL) | 50.9 | (−) | 96.5 | (+) | 100 |
| 4 | Alcaligenes sp. (Lipase PL) | 54.1 | (−) | 84.8 | (+) | 100 |
| 5 | Aspergillus sp. (Lipase AP) | 47.6 | (−) | 87.6 | (+) | 78.6 |
| 6 | Mucor sp. (Lipase M-AP) | 43.5 | (−) | 95.5 | (+) | 70.0 |
| 7 | Rhizopus sp. (Lipase Saiken) | 40.5 | (−) | 85.0 | (+) | 57.5 |
| 8 | Porcine Pancreas (steapsin) | 49.6 | (−) | 100 | (+) | 99.0 |

EXAMPLES 9 TO 15

0.65 g of a capric ester of (±)-propynylcyclopentenolone and 10 mg of each esterase as shown in Table 2 were added to 5 ml of a buffer solution and allowed to react at 30° C. for 24 hours with vigorous stirring using an agitator. Subsequent procedures were similar to those in Examples 1 to 8. The results are shown in Table 2.

TABLE 2

| Example No. | Origin of Esterase | Hydrolysis Rate (%) | Free Propynylcyclopentenolone Optical Isomer Form | Free Propynylcyclopentenolone Optical Purity (%) | Unreacted Ester Optical Isomer Form | Unreacted Ester Optical Purity (%) |
|---|---|---|---|---|---|---|
| 9 | The Arthrobacter sp. (Lipase Godo BSL) | 50.0 | (−) | 100 | (+) | 100 |
| 10 | The Alcaligenes sp. (Lipase PL) | 50.0 | (−) | 100 | (+) | 100 |

TABLE 2-continued

| Example No. | Origin of Esterase | Hydrolysis Rate (%) | Free Propynylcyclopentenolone | | Unreacted Ester | |
|---|---|---|---|---|---|---|
| | | | Optical Isomer Form | Optical Purity (%) | Optical Isomer Form | Optical Purity (%) |
| 11 | The Achromobacter sp. (Lipase AL) | 50.0 | (−) | 100 | (+) | 100 |
| 12 | The Pseudomonas sp. | 47.1 | (−) | 100 | (+) | 88.4 |
| 13 | The Aspergillus sp. (Lipase AP) | 38.8 | (−) | 99.5 | (+) | 60.2 |
| 14 | *Rhizopus delemar* (Talipase) | 35.6 | (−) | 83.0 | (+) | 50.0 |
| 15 | Porcine Pancreas (Steapsin) | 51.1 | (−) | 98.7 | (+) | 100 |

EXAMPLES 16 TO 21

In a 500 ml flask with shoulders was placed 100 ml of a liquid medium (100 ml) [for fungi and yeasts (Examples 20 and 21), a malt extract-yeast extract medium (5.0 g of peptone, 10.0 g of glucose, 3.0 g of malt extract and 3.0 g of yeast extract dissolved in 1 l of water and adjusted to pH 6.5), and for bacteria (Examples 16 to 19), a sugar-added bouillon medium (10.0 g of glucose, 5.0 g of peptone, 5.0 g of meat extract and 3.0 g of NaCl dissolved in 1 l of water and adjusted to pH 7.2)]. After sterilization, the resulting medium was inoculated with two platinum loop-fuls of each slant cultured microorganism as shown in Table 3, and cultured on a reciprocating shaker at 30° C. for 48 hours. Then, to this cultured medium was added 7 g of an acetic acid ester of (±)-propynylcyclopentenolone, followed by reciprocal shaking at 30° C. for 24 hours. Subsequently, the reaction mixture was steam distilled, and the distillate was extracted with diethyl ether. The extract was concentrated, and free propynylcyclopentenolone was separated by the same column chromatography procedure as in Examples 1 to 8. The free propynylcyclopentenolone was subjected to optical isomeric analysis by the same procedure as in Examples 1 to 8. The results are shown in Table 3.

TABLE 3

| Example No. | Microorganisms Used | Hydrolysis Rate (%) | Free Propynylcyclopentenolone | |
|---|---|---|---|---|
| | | | Optical Isomer Form | Optical Purity (%) |
| 16 | *Arthrobacter simplex* IFO 3530 | 49.0 | (−) | 97.0 |
| 17 | *Pseudomonas fluorescens* IFO 3081 | 49.0 | (−) | 100 |
| 18 | *Nocardia asteroides* IFO 3424 | 53.9 | (−) | 86.5 |
| 19 | *Brevibacterium ammoniagenes* IFO 12072 | 30.9 | (+) | 89.1 |
| 20 | *Rhodotorula minuta* IFO 0879 | 45.3 | (−) | 90.2 |
| 21 | *Trichoderma viride* IFO 4847 | 50.2 | (−) | 100 |

EXAMPLE 22

One liter (1 l) of a cultured medium of *Trichoderma viride* IFO-4847 as prepared by the same procedure as in Example 21 was filtered to obtain a culture filtrate. 30 ml of the culture filtrate was concentrated to one-third, and 1.5 g of a formic acid ester of (±)-propynylpentenolone was added thereto, followed by stirring vigorously at 30° C. for 30 hours using an agitator. Subsequent procedures were similar to those in Examples 1 to 8. The results are shown in Table 4.

TABLE 4

| Hydrolysis Rate (%) | Free Propynylcyclopentenolone | | Unreacted Ester | |
|---|---|---|---|---|
| | Optical Isomer Form | Optical Purity (%) | Optical Isomer Form | Optical Purity (%) |
| 50.0 | (−) | 100 | (+) | 100 |

EXAMPLE 23

Microorganism cells were collected by centrifugal separation from 1 l of a cultured medium of *Rhodotorula minuta* IFO 0879 as prepared by the same procedure as in Example 20, washed twice with distilled water, and then lyophilized. 500 mg of the freeze-dried microorganism cells and 1 g of a formic acid ester of (±)-propynylcyclopentenolone were added to 10 ml of a McIlvaine buffer solution of pH 7.0, followed by stirring vigorously at 30° C. for 30 hours using an agitator. Subsequent procedures were similar to those in Examples 1 to 8. The results are shown in Table 5.

TABLE 5

| Hydrolysis Rate (%) | Free Propynylcyclopentenolone | | Unreacted Ester | |
|---|---|---|---|---|
| | Optical Isomer Form | Optical Purity (%) | Optical Isomer Form | Optical Purity (%) |
| 47.3 | (−) | 100 | (+) | 89.0 |

What is claimed is:

1. A biochemical process for optical resolution of (±)-4-hydroxy-3-methyl-2-2'-propynyl-2-cyclopentenone, characterized in that an organic carboxylic acid (saturated or unsaturated carboxylic acids having 1 to 18 carbon atoms) ester of (±)-4-hydroxy-3-methyl-2-2'-propynyl-2-cyclopentenone is reacted with an esterase derived from a microorganism or an animal pancreas, so as to asymmetrically hydrolyze said ester into optically active 4-hydroxy-3-methyl-2-2'-propynyl-2-cyclopentenone and esters of its antipode.

2. A process according to claim 1, wherein the esterase is derived from a microorganism belonging to the genus Enterobacter, Arthrobacter, Brevibacterium, Pseudomonas, Alcaligenes, Flavobacterium, Micrococcus, Chromobacterium, Mycobacterium, Corynebacterium, Bacillus, Lactobacillus, Trichoderma, Candida, Saccharomyces, Rhodotorula, Cryptococcus, Torulopsis, Pihia, Penicillium, Aspergillus, Rhizopus, Mucor, Aureobasidium, Actinomucor, Nocardia, Streptomyces, or Achromobacter.

3. A process according to claim 1, wherein the esterase is derived from a microorganism belonging to the genus Enterobacter, Arthrobacter, Brevibacterium, Pseudomonas, Alcaligenes, Chromobacterium, Mycobacterium, Bacillus, Trichoderma, Candida, Rhodotorula, Torulopsis, Aspergillus, Rhizopus, Mucor, Nocardia, Streptomyces, or Achromobacter.

4. A process according to claim 1, wherein the organic carboxylic acid ester is an ester of acetic acid, capric acid, or formic acid.

5. A process according to claim 1, wherein the organic carboxylic acid ester is an ester of acetic acid.

* * * * *